United States Patent
Kuhrts

(10) Patent No.: US 6,953,593 B2
(45) Date of Patent: Oct. 11, 2005

(54) SUSTAINED-RELEASE MICROENCAPSULATED DELIVERY SYSTEM

(75) Inventor: Eric H. Kuhrts, Bodega, CA (US)

(73) Assignee: Lipoprotein Technologies, Inc., Bodega, CA (US)

( * ) Notice: Subject to any disclaimer, the term of this patent is extended or adjusted under 35 U.S.C. 154(b) by 0 days.

(21) Appl. No.: 09/495,556

(22) Filed: Feb. 1, 2000

(65) Prior Publication Data

US 2002/0098239 A1 Jul. 25, 2002

(51) Int. Cl.$^7$ .............................. A61K 9/14; A61K 9/16
(52) U.S. Cl. ........................ 424/490; 424/489; 424/490; 424/491; 424/498
(58) Field of Search ................................ 424/489, 499, 424/502

(56) References Cited

U.S. PATENT DOCUMENTS

| | | | | |
|---|---|---|---|---|
| 4,837,381 A | * | 6/1989 | Steber et al. ................ | 424/500 |
| 5,494,681 A | * | 2/1996 | Cuca et al. ................. | 424/484 |
| 5,756,719 A | * | 5/1998 | Chaundy et al. ............. | 536/119 |
| 5,849,240 A | * | 12/1998 | Miller et al. ................ | 264/460 |
| 5,958,452 A | * | 9/1999 | Oshlack et al. ............. | 424/457 |
| 6,048,562 A | * | 4/2000 | Mandralis et al. .......... | 426/573 |

* cited by examiner

*Primary Examiner*—Thurman K. Page
*Assistant Examiner*—S. Tran
(74) *Attorney, Agent, or Firm*—Thorpe North & Western, LLP

(57) ABSTRACT

Disclosed is a process for producing sustained-release powders that is fast, efficient, and economical. The process involves melting an animal or vegetable oil with a melting point above 110 degrees F. in specially designed mixer through either the work energy input of the mixer shaft itself, or a specially fitted plow type mixer equipped with a heating tank, cooling unit, jacket for hot water circulation, and heated lines with nozzles for atomizing the hot oil to be sprayed on. The entire manufacturing process can be completed in about 5–30 minutes, and results in small, sustained-release particles that are free flowing and solid at room temperature. The preferred oil is a hydrogenated soy oil with a melting point range of 145–160 degrees F. which is applied at about a 5% level by weight in a high shear mixer. Also included are sustained-release compositions for therapeutic agents such as drugs, botanicals, biological agents, fungicides, and fertilizers.

50 Claims, No Drawings

SUSTAINED-RELEASE MICROENCAPSULATED DELIVERY SYSTEM

BACKGROUND OF THE INVENTION

Field of the Invention

This invention relates to a process for manufacturing pharmaceutical formulations that results in sustained-release microparticles. These microparticles release a therapeutic agent gradually in a consistent fashion over a prolonged period of time, and can be manufactured in a way to yield a high percentage of drug core at a very economical cost. The process consists of heating and mixing a vegetable oil with a very high melting point with a therapeutic agent or drug until well coated, and then cooling to room temperature until hard. The resultant particles are small, free flowing, and exhibit release profiles that can be adjusted to extend from 6–24 hours. Other fibers, sugars, or polymers can be added in layers as an outer coat after cooling to effect the release profile and the hydrophobic properties of the particles, or directly to the matrix to accelerate drug release by creating additional channels for diffusion during erosion while dissolving. Other substances such as minerals can be added to the cores to provide additional weight to the particles causing them to sink due to heaviness.

The benefits of producing sustained-release formulations of drugs or other therapeutic agents is now widely recognized in the medical literature and is utilized in many commercial products. It is important to distinguish at the out-set between solid monolithic dosage forms such as tablets, and powders, and particles that are loosely packed into capsules. A sustained-release powder consists of microparticles that are microencapsulated using a manufacturing process that enables them to be ingested, as, for example a powdered drink-mix which can be added to a liquid and still retain its sustained-release and taste masking properties, or encapsulated in two piece hard shell gelatin capsules. Microencapsuled powders may behave differently when subjected to the high pressures required to form tablets, and may fracture in the process. In addition, sustained-release tablet formulations may employ other techniques that emanate from their large size, surface area and the swelling properties of hydrocolloids. In this case, diffusion and solubility issues become important for sustained-release.

In the present invention, the drug particles are processed in a way to yield a high percentage of active component powder that is still small enough to be virtually indistinguishable from the original drug particles themselves. Surprisingly, drug cores consisting of 95% of the active agent are possible that release over a full 24-hour period.

In general, sustained-release dosage forms are multi-particle formulations that when ingested in capsule form, rapidly disintegrate into a large number of subunits. This is fine for drugs that are effective at relatively low doses, or dose levels that can fit into a capsule that is a reasonable size. The amount of drug that can fit into a two piece hard shell capsule that is easy for most people to swallow is at most about 800 mg. based on bulk density of the compound. But when large doses are required, such as for example with nutraceuticals, amino acids, or botanical substances, it is desirable to take them in a powder dosage form that can be mixed with a liquid and consumed.

There are many different ways to microencapsulate drugs producing sustained-release. Many of these methods can be found in "Microcapsules and Microencapsulation Techniques", 1976, M. H. Goucho, and Microcapsules and other Capsules, 1979, also by M. H. Goucho. Another resource book is "Aqueous Polymeric Coatings For Pharmaceutical Dosage Forms", 1989, Marcel Dekker, Inc. Most of the methods of producing sustained-release microparticles can be classified into either physical or chemical systems. Physical methods would include such techniques as pan coating, gravity-flow, centrifuge, and the Wurster Process. The Wurster Process employs a high velocity air stream that is directed through a cylindrical fluid bed in which the particles are suspended in the air. A coating is sprayed onto the suspended particles, and the particles flow out the top of the cylinder and descend back to the layer of fluid. The flow of air-dries the coating, so that successive layers can be applied repeatedly by further spraying. Variables that control the process include the number of cycles, temperature, pressure, and humidity, and can be used to provide the desired coating composition and thickness.

Chemical methods of microencapsulation are usually coacervation or phase separation. This technique involves dissolving the membrane forming polymer in a suitable solvent or vehicle and the drug to be dissolved is suspended in this solution and kept under agitation The coating precipitates onto a droplet of the drug, similar to crystallization.

Fluid bed granulation or coating is one of the most common techniques used at the present time for small particle sustained-release. Fluidized bed equipment is available as "top spray","bottom spray", and "tangential-spray". The core drug is first preheated in the vessel to about 30° C. with hot air, placing the particles in suspension. The floating particles are then sprayed with an aqueous suspension to provide a coating, while drying at the same time. Inlet temperature, spray rate, and air throughput must be adjusted to provide optimum end product. Furthermore, the finished particles must be subjected to a post-drying period at around 40° C., where any residual moisture can be driven off. In some case, this last drying period may be up to 24 hours.

Many of the polymers that are used to provide sustained-release properties to powders in the fluid bed process require solvents such as acetone, isopropyl alcohol, chlorinated solvents, alkanes, methyl ethyl ketone, cyclohexane, toluene, carbon tetrachloride, chloroform, and the like. Evaporation of the solvents becomes an environmental concern, and in many states it is illegal to release these emissions into the atmosphere. Aqueous or water based polymers are limited mainly to ethyl cellulose and methacrylic acid esters such as poly methacrylate dispersions. In addition, 10–20% of a suitable plasticizer such as triethyl citrate must be added to the polymer. For example, U.S. Pat. No. 5,603,957 uses a solvent-based polymer system to deliver aspirin over a 24-hour period. Prefered solvents are acetone/alkanol mixtures, or cyclohexane, toluene, or carbon tetrachloride. Castor oil, a low melting point oil, is also included in the polymer solvent mix.

Typical aqueous ethyl cellulose polymers currently in wide use include; Surelease®, Colorcon, West Point, Pa., and Aquacoat®, FMC Corporation, Philadelphia, Pa. In the Aquacoat® brochure available on their web site, it is recommended that for sustained-release applications, at least a two hour curing time at 60° C. be conducted to insure reproducible release profiles. This should be done in a tray dryer. Subjecting drugs and other therapeutic compounds such as botanical extracts to 60° C. temperatures for 2 hours or more is likely to result in a loss of potency or degradation of active principles, and is especially problematic for substances with low melting points. Botanical extracts, in particular, have many volatile compounds that can be destroyed if kept at high temperatures for long periods.

Another polymer in common use for sustained-release applications is Eudragit®, Huls America, Somerset N.J. This is a neutral methacrylic acid ester with a small proportion of trimethylammonioethyl methacrylate chloride. This polymer is also applied using the fluid bed process, or can be used in a standard wet granulation procedure. Wet granulation involves mixing the drug or therapeutic agent with water in a conventional high-speed mixer until a pasty mass, and then dried in an oven over 24 hours at 60° C.

Wet granulations have the additional draw back in that they can effect the potency of botanical extracts by causing instability, or transformation. In addition, when dried at 60° C., many sensitive active principles are lost.

Carnauba wax has also been used to produce sustained-release dosage forms. Usually, at least a 15% level of wax is applied to the drug for the core, followed by a further coat of ethyl cellulose and polyvinylpyrrolidone (PVP) at about 10 to 15% by weight. This results in drug levels in the cores that range from 50 to 70%, with the other 50 to 30% being the wax and polymers.

Synthetic waxes are also available such as Syncrowax®, available from Croda Inc., Parsippany, N.J. These triglyceride waxes have properties similar to carnauba wax, and have melting points of 60–75° C.

Another method of producing sustained-release particles is by starting with sugar spheres or nonpareils. The sugar spheres are also processed in a fluid bed granulator, but the drug must be dissolved in a aqueous solution and sprayed onto the sugar spheres, followed by spray coating with polymers that produce sustained-release as previously mentioned. This system results in large particles that are not acceptable in most drink mix applications, and botanical extracts cannot be dissolved enough to use in this system. The therapeutic agent needs to be absorbed into the sugar particle. The smallest starting particle size for non-pareils is about 60 mesh (US standard sieve number). After coating, the particles are often 30 mesh and larger. The large particle size also presents a problem when encapsulating or tableting.

Melt-spinning techniques involve subjecting a therapeutic agent to sustained heat treatment with a melted polymer which is pumped at a constant rate under high pressure through a plate having a number of small holes, referred to as a spinneret. Filaments emerge from the spinneret into air where they are cooled. These filaments are made into sustained-release formulations. In this process, a polymer is melted on a hot grid or by extrusion-type screw, and then passed to a metered pump. U.S. Pat. Nos. 5,445,769 and 5,458,823 describe the use of a type of melt-spinning technique called a liquiflash spheronization or liquiflash microspheres. Temperatures as high as 130–240 degrees C. are often required in this process. In addition, the polymers for the final coats are dissolved in solvents such as acetone and sprayed onto the microshperes in a fluidized bed apparatus with a Wurster column.

U.S. Pat. No. 5,700,471 involves subjecting an aqueous dispersion of a drug or dye to turbulent mixing at a temperature that is above the melting point of the dye or drug, producing a melt emulsion which is then spray dried or converted into a suspension by cooling.

A hot melt technique is described in U.S. Pat. No. 5,718,921 in which a polymer is dissolved in a volatile organic solvent, and the drug is dispersed or dissolved in the polymer solution. The mixture is then suspended in an organic oil, and the organic solvent is extracted into the oil, creating microspheres. In this process, silicon oil, vegatable oil, paraffin, and mineral oil are used. These are all low melting point oils.

U.S. Pat. No. 4,855,326 discloses combining sugar with low melting point oils such as vegetable oil, baby oil, margarine, cocoa butter and the like to help over come hydrophobic properties and facilitate dispersion in water. None of the oils are solid at room temperatures or have high melting points. The oils themselves are not providing sustained-release properties.

In another process, ethyl cellulose, polyvidone and a small amount of castor oil are dissolved in acetone and isopropanol and sprayed onto aspirin particles in a fluid bed granulator such as is described in U.S. Pat. No. 5,603,957. In this case the oil is liquid at room temperatures, and is being used as a plasticizer. The polymers are providing the sustained-release properties, not the oil. Castor oil itself cannot be used as a solid coating material because of its low melting point.

SUMMARY OF THE INVENTION

It is the object of the present invention to provide a sustained-release microencapsulation process that can be produced inexpensively and quickly and result in a very high percentage of active substance in the core. It is a further advantage of the instant invention not to necessitate the use of solvents or synthetic polymers, although polymers can be used as an additional means of control if desired. It is a further advantage of the present invention not to require extremely high temperatures to produce the microspheres, and to shorten the length of time the materials are processed or exposed to elevated temperatures.

In accordance with the invention, there is provided a microsphere that is produced by mixing the therapeutic agent with a hot vegetable oil with a melting point at least above 110° C., and preferably about 160 degrees F., in a vertical or horizontal high intensity shear mixer until the particles or the core substance are thoroughly mixed with the oil, and then cooling the hot melt to produce fine particles that exhibit excellent sustained-release properties. Surprisingly, the entire process can be completed in about 10 minutes or less, utilizing the work input of the mixer to melt the oil and intimately mix it with the core agent. The ideal high temperature melting point oil for this process is a hydrogenated soy oil with a maximum iodine value of 5.0 and a melting point of 150–160° C. Such an oil with these specifications is Dritex S® in flake form or Sterotex HM® which is a spray chilled, powder. Both are available from AC Humko, Memphis Tenn. The melting point profile is more uniform if the spray chilled powder is used.

The apparatus that is used to manufacture the powder can be a Littleford vertical or horizontal high intensity mixer (LittleforDay, Florence Ky.), or a standard Hobart type mixer or plow mixer that is jacketed with a hot water bath If the Littleford high intensity shear mixer is used, the oil or fat is melted by the work input from the mixer itself, which is a screw type auger shaft that resides within the vessel. The unique mixing action of the auger shaft revolving at a high rate of speed causes the particles to fluidize in free space, providing a high volume rate of material transfer throughout the entire length of the vessel. This results in the mixing, blending and melting of the oil with the other core materials all in the same process and within minutes. The vessel is also jacketed so it can be kept at the melting point temperature of the oil. In addition, the vessel can be fitted with high speed impact choppers to enhance mixing and or drying. After processing this way, the material is cooled and discharged as a free flowing powder.

If desired, the molten oil can be sprayed on from a heating tank fitted with heated insulated lines using a tower-mounted, hydraulic atomizing nozzle. If sprayed onto the core material, the work input is not needed to melt the oil because it is already melted, and less shear is needed. This results in less compaction of the particles because more shear results in harder particles. In some cases this may be desirable for shorter release profiles. Surprisingly, the high shear mixer with good compaction of the oil/core particles can result in sustained-release profiles that span over 24 hours with only a 3–5% by weight oil level. In other words, 95–97% of the powder is the core material. This sustained-release powder is of fine particle size and exhibits excellent flow properties, and may be used as a food additive, incorporated into a powdered drink mix, or manufactured into solid dosage forms.

DETAILED DESCRIPTION OF THE INVENTION

While oils have been used in various sustained-release formulations, they are usually not the primary material that is providing the barrier to gastric erosion, or the coating material to microencapsulate the substance. Most of the oils used are liquid or soft at room temperature.

Oils such as low melting point vegetable oil, caster oil, baby oil, margarine, cocoa butter, paraffin, and the like have also been used in the pharmaceutical industry for a variety of purposes, but not as sustained-release agents. For example, soft oils are often used for suppositories. These oils cannot be used to provide solid particles at room temperature. Various resins and shellac have also been used, but usually not for sustained-release. Carnauba wax is widely used in pharmaceutical dosage forms.

An oil such as a hydrogenated soy oil with an iodine value of at about 5, and a melting point above 120 degrees F., will be solid at room temperatures. In fact, such an oil or fat with a melting point above 145 degrees F. will allow melting to occur only at temperatures that are significantly above those temperatures normally encountered by food or pharmaceutical products, even during shipment on hot days. Just such an oil is Sterotex HM®, manufactured by AC Humko, Memphis Tenn., a spray chilled hydrogenated soy oil that completely melts at about 160° F. This oil is completely solid at lower temperatures, and is available as a powder. Other oils of similar melting points are available, but are usually in a solid mass, and must be chiseled or chipped apart, and therefore are difficult to use and weigh out. Some oils are available in flake form such as Dritex S from the same company. Either product is preferable to the solid mass hydrogenated soy oils. Any oil with a melting point above about 110° F. will work, but the most desirable would be those oils with melting points from 120–200° F., and ideally about 120–180° F. These melting points are usually below the melting point of most drugs or therapeutic compounds, and are achievable using the above described equipment.

Animal or vegetable oils may be used in the present invention. Such oils may have a melting point between 120 degrees F. and 200 degrees F. In one embodiment, the oils may have a melting point of 110–200 degrees F. In another embodiment, the oils may have a melting point of 120–180 degrees F. For example, hydrogenated soy oil having a melting point of about 160 degrees F. may be used. Hydrogenated soy oil may also have a melting point in the range of about 145–160 degrees F. Another example of an oil for use in the present invention is hydrogenated vegetable oil with a melting point above 110 degrees F.

Natural oils such as soy oil or other vegetable oils are most preferred. These oils are very acceptable to health conscious consumers, and appear user friendly on the label. Stearic acid is an oil that is derived from either animal or vegetable sources and has a melting point of about 70° C. USP stearic acid is primarily a mixture of stearic and palmitic acids.

The oils used in the present invention may be provided in an amount such that the finished sustained-release particle contains oil in about 3% to 50% by weight of the finished particle. In another aspect of the present invention, the particle may contain oil in about 5% to 30% by weight of the finished particle. The particle may also contain oil in about 3% to 20% by weight of the finished particle. In another aspect of the present invention, the particle may contain oil in about 3% to 10% by weight of the finished particle. Thus, the particle may contain oil in about 5% by weight of the finished particle.

The core material may be selected from any suitable drug, therapeutic or prophylactic agent, nutritional agent, biological substance, fungicide, food or botanical substance, fertilizer, or animal feed, which can be incorporated in the hot melt without losing substantial activity for the chosen therapy. A broad range of materials is therefore useful. Representative non-limiting classes of drugs or nutritional agents useful include those falling into the following therapeutic categories:

Ace-inhibitors; anti-anginal drugs; anti-arrhythmias; anti-asthmatics; anti-cholesterolemics; anti-convulsants; anti-depressants; anti-diarrhea preparations; anti-histamines; anti-hypertensive drugs; anti-infectives; anti-inflammatory agents; anti-lipid agents; anti-manics; anti-nauseants; anti-stroke agents; anti-thyroid preparations; anti-tumor drugs; anti-tussives; anti- uricernic drugs; anti-viral agents; acne drugs; alkaloids; amino acid preparations; anabolic drugs; analgesics; anesthetics; angiogenesis inhibitors; antacids; antiarthritics; antibiotics; anticoagulants; antiemetics; anti-obesity drugs; antiparasitics; antipsychotics; antipyretics; antispasmodics; antithrombotic drugs; anxiolytic agents; appetite stimulants; appetite suppressants; beta blocking agents; botanical substances, bronchodilators; cardiovascular agents; cerebral dilators; chelating agents; cholecystokinin antagonists; chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastro-intestinal agents; growth regulators; hormone replacement agents; hyperglycemic agents; hypnotics; hypoglycemic agents; laxatives; migrain treatments; mineral supplements; mucolytics; narcotics; neuroleptics; neuromuscular drugs; NSAIDS; nutritional additives; peripheral vaso-dilators; polypeptides; prostaglandins; psychotropics; renin inhibitors; respiratory stimulants; steroids; stimulants; sympatholytics; thyroid preparations; tranquilizers; uterine relaxants; vaginal preparations; vaso- constrictors; vago-dilators; vertigo agents; vitamins; wound healing agents.

Non-limiting examples of specific therapeutic agents which may be useful in the present invention can be chosen from the list which follows. Mixtures of these agents and their salts used for appropriate therapies are also contemplated: acetaminophen; acetic acid, acetylsalicylic acid and its buffered form; albuterol and its sulfate; alcohol; alkaline phosphatase; allantoin; aloe; aluminum acetate, carbonate, chlorohydrate, hydroxide-alprozolam; amino acids; aminobenzoic acid; amoxicillin; ampicillin; ansacrine; amsalog; anethole; ascorbic acid; aspartame; aspirin; atenolol; bacitracin; balsam peru; BCNU (carmustine) beclomethasone dipropionate; benzocaine; benzoic acid; benzophenones; benzoyl peroxide; bethanechol; biotin; bisacodyl; bomyl acetate; bromopheniramine maleate; buspirone; caffeine; calamine; calcium; calcium carbonate; casinate and hydroxide; camphor, captopril; cascara sagrada; castor oil; cefaclor, cefadroxil; cephalexin; cetylalcohol; cetylpyridinium chloride; chelated minerals; chloramphenicol; chlorcyclizine hydrochloride; chlorhexidine gluconate; chloroxylenol; chloropentostatin; chlorpheniramine maleate; cholestyramine resin; choline bitartrate; chondrogenic stimulating protein; cirnetidine hydrochloride; cinnamedrine hydrochloride; citalopram; citric acid; cocoa butter; cod liver oil; codeine and codeine phosphate; clonidine and its hydrochloride salt, clorfibrate; cortisone acetate; ciprofloxacin HCl; cyanocobalamin; cyclizine hydrochloride; danthron; dexbrompheniranime maleate; dextromethorphan hydrobromide; diazaparn; dibucaine; diclofenac sodium; digoxin; diltiazem; dimethicone; dioxybenzone; diphenhydramine citrate; diphenhydramine hydrochloride; docusate calicurn, potassium and sodium; doxycycline hyclate; doxylamine succinate; efaroxan; enalpril; enoxacin; erythromycin; estropipate; ethinyl estradiol; ephedrine; epinephrine bitartrate; erythropoictin; eucalyptol; ferrous fiamarate, gluconate and sulfate; folic acid; fosphenytoin; 5-fluorouracil (5-FU) fluoxetine HCl; furosemide; gabapentan; gentarnicin.-gemfibrozil; glipizide; glycerin; glyceryl stearate; griseofulvin; growth hormone; guaifenesin; hexylresorcinol; hydrochlorothiaxide; hydrocodone bitartrate; hydrocortisone and its acetate; 8-hydroxyquinoline sulfate; ibuprofen; indomethacin; inositol; insulin; iodine; ipecac-, iron; isoxican; ketamine; kaolin; lactic acid; lanolin; lecithin; leuprolide acetate; lidocaine and its hydrochloride salt; lifinopril; liotrix; lovastatin; luteinizing hormone; LHRH (luteinizing hormone releasing hormone).- magnesium carbonate, hydroxide, salicylate; trisilocate; mefenamic acid; meclofenanic acid; meclofenamate sodium; medroxyprogesterone acetate; methenamine mandelate; menthol; meperidine hydrochloride; metaproterenol sulfate; methyl nicotinate; methyl salicylate; methylcellulose; methsuximide; metronidazole and its hydrochloride; metoprolol tartrate; miconazole nitrate; mineral oil; minoxidil; morphine; naproxen and its sodium salt; nifedipine; neomycin sulfate; niacin; niacinamide; nicotine; nicotinamide; nitroglycerin; nonoxynol-9; norethindone and its acetate; nystatin; octoxynol; octoxynol 9; octyl dimethyl PABA, octyl. methoxycinnamate; omega-3 polyunsaturated fatty acids; omeprazole; oxolinic acid; oxybenzone; oxtriphylfine; para-aminobenzoic acid (PABA); padimate 0; paramethadoine; pentastatin; peppermint oil; pentaerythriol tetranitrate; pentobarbital sodium; pheniramine maleate; phenobarbital; phenol; phenolphthalein; phenylephrine hydrochloride; phenylpropanolamine and its hydrochloride salt; phenytoin; phenelzine sulfate; pirmenol; piroxicam; polymycin B sulfate; potassium chloride and nitrate; prazepam; procainamide hydrochloride; procaterol; propoxyphene and its HCI salt; propoxyphene napsylate; pramiracetin; pramoxine and ita hydrochloride salt propronolol HCl; pseudoephedrine hydrochloride and sulfate; pyridoxine; quinapril; quinidine gluconate and sulfate; quinestrol; ralitoline; ranitidine; resorcinol; riboflavin; salicylic acid; sesame oil; shark liver oil; simethicone; sodium bicarbonate; citrate and fluoride; sodium monofluorophosphate; sucralfate; sulfanethoxazole; sulfasalazine; sulfer; tacrine and its HCI salt; theophylline; terfenidine; thioperidone; trimethrexate; triazolam; timolol maleate; tretinoin; tetracycline hydrochloride; tolmetin; tolnaftate; triclosan; triprolidine hydrochloride; undecylenic acid; vancomycin; verapamil HCl; vidaribine phosphate; vitamins A, B., C., D, B-1, B2, B 6, B12, E, K; witch hazel; xylometazoline hydrochloride; zinc; zinc sulfate; zinc undecylenate.

Useful dosage forms include without limitation oral forms such as tablets, capsules, beads, granules, aggregates, powders, gels, solids, semi-solids, and suspensions. Injectable forms, lotions, transdermal delivery systems including dermal patches, implantable forms or devices, aerosols or nasal mists, suppositories, salves and ointments are also useful.

The inventive compositions have great versatility in their application. The compositions can be used for wound management such as by direct application to burns, abrasions, skin diseases or infections and the like. Other uses such as packing agents for nasal wounds or other open wounds are also contemplated.

In certain preferred embodiments, an amino acid like substance such as L-arginine, or L-carnitine, sports supplements such as creatine monohydrate, a vitamin such as niacin or vitamin C may be the core material. A therapeutic substance such as garlic powder, astaxanthin, or polygonum cuspidatum root extract would be examples of botanical substances. Also in this category would be tocotrienols or co-enzyme Q-10. An anti-histamine such as loratadine would be desirable in a 24 hour release profile. Blood pressure medication is also a preferred class of drugs. Fertilizers and fungicides would be non-drug applications for the process. Slow release of fertilizers and fungicides in the soil is especially desirable for nitrogen containing formulas. In a sustained-release microcapsule, the nitrogen fertilizer will tend not to leach out of the soil when wet.

A variety of additives can be incorporated into the inventive compositions for their intended functions. These additives are usually used in small amounts. In some cases, additives such as hydrocolloids are used as suspending agents, as for example in a powdered drink mix that is reconstituted in liquid.

Useful additives include, for example, gelatin, vegetable proteins such as sunflower protein, soybean proteins, cotton seed proteins, peanut proteins, rape seed proteins, blood proteins, egg proteins, acrylated proteins; water-soluble polysaccharides such as alginates, carrageenans, guar gum, agar-agar, gum arabic, and related gums (gum ghatti, gum karaya, gum tragacanth), pectin, water-soluble derivatives of cellulose: alkylcelluloses, hydroxyalkyl celluloses and hydroxyalkylalkylcelluloses, such as methylcellulose, hydroxymethylcellulose, hydroxyethylcellulose, hydroxypropylcellulose, hydroxyethylmethylcellulose, hydroxpropylmethylcelluose, hydroxbutylmethylcellulose, cellulose esters and hydroxyalkylcellulose esters such as: cellulose acetate phthalate (CAP), carboxyalky I celluloses, carboxyalkylalkylcelluloscs, carboxyalkylcellulose esters such as carboxymethyl cellulose and their alkali metal salts; water-soluble synthetic polymers such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone (PVP), PVP/vinyl acetate copolymer, and polycrotonic acids; also suitable are phthalated gelatin, gelatin succinate, crosslinked gelatin, shellac, water-soluable chemical derivatives of starch, cationically modified acrylates and methacrylates possessing, for example, a tertiary or quaternary amino group, such as the diethylaminoethyl group, which may be quatemized if desired; and other similar polymers.

Processing aids such as sucrose, polydextrose, dextrose, maltodextrin, lactose, maltose, and the like may also be used. In some cases where accelerated release is desired, a sugar may be incorporated into the hot melt. Since the oil coating is hydrophobic, incorporating a hydrophilic sugar in the hot melt helps counteract the tendency of the particles to float. The sugar also helps to increase the rate of release of the core material by providing solubility to the matrix. Sugar may be present in the melt from 1–30% by weight of the finished particles. In some embodiments of the present invention, the sugar is present in the melt from 5–20% by weight of the finished particles. For example, the sugar may be present in the melt at about 10% by weight of the finished particles. Other substances such as calcium carbonate or other minerals can be added to provide weight to the partiales and affect the release profile.

A mineral may also be present in the melt from 1–20% by weight of the finished particles. In some embodiments of the present invention, the mineral may be present in die melt from 5–10% by weight of the finished particle. For example, calcium carbonate may be provided in the melt at about 5% by weight of the finished particle.

Examples of classes of additives includes excipients, lubricants, hydrocolloid suspending agents, buffering agents, disintegrating agents, stabilizers, foaming agents, pigments, coloring agents, fillers, bulking agents, sweetening agents, flavoring agents, fragrances, release modifiers, etc.

EXAMPLES

Example 1

Niacin (nicotinic acid) is added to a plow mixer, which was capable of operating at high temperatures because it was jacketed with a second layer to allow hot water to flow around the vessel. The unit was fitted with a tower-mounted, hydraulic atomizing nozzle with heated tanks and heated/insulated lines to enable hot oil to be applied at high temperarures. A high speed chopper operating at 10 hp was fitted at the discharge point. Hydrogenated soy oil flakes (Dritex S®, AC Humko, Memphis, Tenn.) with a melting point of about 80° C. or 140–160° C. was sprayed on the powder as it was mixing in vessel. Efficient coating or microencapsulation of the powder was achieved in about 30 minutes when a temperature of about 155° F. was reached and the hot oil thoroughly mixed with the powder. Cooling was achieved by discharging the batch into a cooler mounted directly below the mixer. The resulting granules were small, free flowing, and exhibited sustained-release properties when a dissolution test was conducted. The weight percent of the niacin in the finighed product was 90% and the hydrogenated soy oil was 10%.

Dissolution Test

Protocol: Basket method

Media: water

Paddle speed: 50 RPM

Time points/% released: 1 hr-28%, 2hr-38%, 3hr-44%, and 6 hours-45%

Example 2

The amino acid L-arginine free base, was charged to a Littleford W-10 high shear mixer with a hot water jacket to allow circulating hot water to keep the vessel hot. After mixing for 1 minute at 1000 RPM, spray chilled hydrogenated soy oil powder(Sterotex HM®, AC Humko, Memphis Tenn.) was added to the vessel. The work input was increased to 2000 RPM and then adjusted down to about 600 RPM for 5 minutes. The high shear of the mixer melted the oil and mixed with the core ingredients. Surprisingly, the work input of the mixer itself provided enough energy to melt the oil without the need of a heating tank and lines to spray the hot oil as in the previous example. The powder was discharged into a cooler mounted below the unit. The resulting particles were small, powder like, free flowing, and exhibited excellent sustained-release properties with a 24 hour release profile at only a 5% by weight of oil.

| Dissolution test 95% L-arginine free base/5% hydrogenated soy oil | |
|---|---|
| L-arginine base assay | 100% |
| Time Release Pattern | |
| 1 hour | 20% |
| 2 hrs | 23% |
| 4 hrs | 30% |
| 6 hrs | 35% |
| 8 hrs | 40% |
| 16 hrs | 70% |
| 24 hrs | 100% |

Example 3

Creatine monohydrate is charged to a Littleford high shear mixer with calcium carbonate (5% by weight) and sucrose (10% by weight) and mixed at 1000 RPM. Sterotex HM® hydrogenated soy oil is added at a 5% level and the speed of rotation is increased to 2000 RPM to melt the oil, and then decreased to maintain the power draw to within the allowable motor amperage. Unexpectedly, after 3–5 minutes the oil is fully melted and mixed with the core materials, and upon inspection, the batch is fully granulated. The powder is discharged into the cooling unit and appears as a fine granular, free flowing sustained-release powder.

| Dissolution Test | |
|---|---|
| Formulation: | |
| Creatine monohydrate | 80% |
| Sucrose | 10% |
| Calcium Carbonate | 5% |
| Hydrogenated soy oil (Sterotex HM ®) | 5% |
| Time Release Pattern: | |
| 1 hour | 46% |
| 2 hrs | 63% |
| 4 hrs | 78% |
| 6 hrs | 85% |
| 10 hrs | 100% |

While the present invention is described above in connection with the preferred or illustrative embodiments, those embodiments are not intended to be exhaustive or limiting of the invention, but rather, the invention is intended to cover any alternatives, modifications or equivalents that may be included within its scope as defined by the appended claims.

What is claimed is:

1. A microencapsulaton process comprising:
   a) adding a core material and a vegetable oil having a melting point between 120 degree F. and 200 degree F. into a high shear mixer;

b) mixing the core material and the oil until microencapsulated particles are formed in the high shear mixer that comprise the core material and the oil, said microencapsulated particles being formed without dissolving or dispersing the core material or oil with solvent; and c) discharging the microencapsulated particles as a powder from the high shear mixer;

with the proviso that no classification step is performed during the microencapsulation process.

2. The microencapsulation process of claim 1, further comprising the step of cooling the microencapsulated particles.

3. The microencapsulation process of claim 1, wherein mixing the core material and the vegetable oil comprises mixing at a mixer work input sufficient to melt the oil.

4. The microencapsulation process of claim 1, wherein the mixer comprises a heated jacket, and wherein the heated jacket heats the mixer sufficiently to melt the vegetable oil upon addition of the oil to the mixer.

5. The microencapsulation process of claim 1, wherein the core material comprises ace-inhibitors; anti-anginal drugs; anti-arrhythmias; anti-asthmatics; anti-cholesterolemics; anti-convulsants; anti-depressants; anti-diarrhea preparations; anti-histamines; anti-hypertensive drugs; anti-infectives; anti-inflammatory agents; anti-lipid agents; anti-manics; anti-nauseants, anti-stroke agents; anti-thyroid preparations; anti-tumor drugs; anti-tussives; anti-uricernic drugs; anti-viral agents; acne drugs; alkaloids; amino acid preparations; anabolic drugs; analgesics; anesthetics; angiogenesis inhibitors; antacids; antiarthritics; antibiotics; anticoagulants; antiemetics; antiobesity drugs; antiparasitics; antipsychotics; antipyretics; antispasmodics; antithrombotic drugs; anxiolytic agents; appetite stimulants; appetite suppressants; beta blocking agents; bronchodilators; cardiovascular agents; cerebral dilators; chelating agents; cholecystokinin antagonists; chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastro-intestinal agents; growth regulators; hormone replacement agents; hyperglycemic agents; hypnotics; hypoglycemic agents; laxatives; migrain treatments; mineral supplements; mucolytics; narcotics; neuroleptics; neuromuscular drugs; NSAIDS; nutritional additives; peripheral vaso-dilators; polypeptides; prostaglandins; psychotropics; renin inhibitors; respiratory stimulants; steroids; stimulants; sympatholytics; thyroid preparations; tranquilizers; uterine relaxants; vaginal preparations; vaso-constrictors; vasodilators; vertigo agents; vitamins; wound healing agents; botanical substances; fungicides, fertilizers, macrn, L-arginine, creatine monohydrate, L-camitine, aspirin, loratidine, lovastatin, vitamin C, garlic powder, polygonum cuspidatum root extrart, astaxanthin, tocotrienol or co-enzyme Q-10.

6. The microencapsulation process of claim 1, wherein the vegetable oil is a hydrogenated soy oil with a melting point of about 160 degrees F.

7. The microencapsulation process of claim 1, wherein the vegetable oil is present in an amount from 3% to 30% by weight in the finished microencapsulated particle.

8. The microencapsulation process of claim 1, wherein the vegetable oil is present in an amount from 3% to 20% by weight in the finished microencapsulated particle.

9. The microencapsulation process of claim 1, wherein the vegetable oil is present in an amount from 3% to 10% by weight in the finished microencapsulated particle.

10. The microencapsulation process of claim 1, wherein mixing the core material and the vegetable oil further comprises mixing a sugar or a mineral with the core material and the vegetable oil.

11. The microencapsulation process of claim 10, wherein the sugar is present in the melt from 1–30% by weight of finished microencapsulated particles.

12. The microencapsulation process of claim 10, wherein the sugar is selected from the following; sucrose, dextrose, lactose, polydextrose, maltodextrin, and maltose.

13. The microencapsulation process of claim 10, wherein the mineral is present in the melt from 1–20% by weight of the finished microencapsulated particles.

14. A microencapsulation process comprising:

a) adding a core material, and a vegetable oil having a melting point between 120 degree F. and 200 degree F. into a high shear mixer;

b) simultaneously fluidizing and mixing the core material and the oil until microencapsulated particles are formed in the high shear mixer that comprise the core material and the oil, said microencapsulated particles being formed without dissolving or dispersing the core material or oil with solvent; and c) discharging the microencapsulated particles as a powder from the high shear mixer.

15. The microencapsulation process of claim 14, wherein the fluidizing and mixing of the core material and the vegetable oil are performed using a screw auger.

16. The microencapsulation process of claim 14, wherein discharging the microencapsulated particles comprises cooling the microencapsulated particles.

17. The microencapsulation process of claim 14, wherein mixing the core material and the vegetable oil comprises mixing at a mixer work input sufficient to melt the oil.

18. The microencapsulation process of claim 14, wherein the mixer comprises a heated jack, and wherein the heated jacket heats the mixer sufficiently to melt the oil upon addition of the vegetable oil to the mixer.

19. The microencapsulation process of claim 14, wherein the core material is selected from the group consisting of ace-inhibitors; anti-anginal drugs; anti-arrhythmias; anti-asthmatics; anti-cholesterolemics anti-convulsants; anti-depressants; anti-diarrhea preparations; anti-histamines; anti-hypertensive drugs; anti-infectives; anti-inflammatory agents; anti-lipid agents; anti-manics; anti-nauseants; anti-stroke agents; anti-thyroid preparations; anti-tumor drugs; anti-tussives; anti-uricernic drugs; anti-viral agents; acne drugs; alkaloids; amino acid preparations; anabolic drugs; analgesics; anesthetics; angiogenesis inhibitors; antacids; antiarthritics; antibiotics; anticoagulants; antiemetics; antiobesity drugs; antiparasitics; antipsychotics; antipyretics; antispasmodics; antithrombotic drugs; anxiolytic agents; appetite stimulants; appetite suppressants; beta blocking agents; bronchodilators; cardiovascular agents; cerebral dilators; chelating agents; cholecystokinin antagonists; chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastro-intestinal agents; growth regulators; hormone replacement agents; hyperglycemic agents; hypnotics; hypoglycemic agents; laxatives; migrain treatments; mineral supplements; mucolytics; narcotics; neuroleptics; neuromuscular drugs; NSAIDS; nutritional additives; peripheral vaso-dilators; polypeptides; prostaglandins; psychotropics; renin inhibitors; respiratory stimulants; steroids; stimulants; syinpatholytics; thyroid preparations; tranquilizers; uterine relaxants; vaginal preparations; vaso-constrictors; vaso-dilators; vertigo agents; vitamins; wound healing agents; botanical substances; fungicides; fertilizers; niacin; L-arginine; creatine monohydrate; L-carnitine; aspirin; loratidine; lovastatin; vitamin C; garlic powder; polygonum cuspidatum root extract; astaxanthin; tocotrienol and co-enzyme Q-10.

20. The microencapsulation process of claim 14, wherein the vegetable oil is a hydrogenated soy oil with a melting point of about 160 degrees F.

21. The microencapsulation process of claim 14, wherein the vegetable oil is present in an amount from 3% to 30% by weight in the finished microencapsulated particle.

22. The microencapsulation process of claim 14, wherein the vegetable oil is present in an amount from 3% to 20% by weight in the finished microencapsulated particle.

23. The microencapsulation process of claim 14, wherein the vegetable oil is present in an amount from 3% to 10% by weight in the finished microencapsulated particle.

24. The microencapsulation process of claim 14, wherein mixing the core material and the vegetable oil further comprises mixing a sugar or a mineral with the core material and the vegetable oil.

25. The microencapsulation process of claim 24, wherein the sugar is present in the melt from 1–30% by weight of finished microencapsulated particles.

26. The microencapsulation process of claim 24, wherein the sugar is selected from the following: sucrose, dextrose, lactose, polydextrose, maltodextrin, and maltose.

27. The microencapsulation process of claim 24, wherein the mineral is present in the melt from 1–20% by weight of the finished microencapsulated particles.

28. A microencapsulaton process comprising:
a) adding a core material, and a vegetable oil having a melting point between 120 degree F. and 200 degree F. into a high shear mixer;
b) mixing the core material and the oil, at a mixer work input ranging from 600 RPM to 2000 RPM, until microencapsulated particles are formed in the high shear mixer that comprise the core material and the oil, said microencapsulated particles being formed without dissolving or dispersing the core material or oil with solvent; and
c) discharging the microencapsulated particles as a powder from the high shear mixer.

29. The microencapsulation process of claim 28, further comprising the step of cooling the microencapsulated particles.

30. The microencapsulation process of claim 28, wherein mixing the core material and the vegetable oil comprises mixing at a mixer work input sufficient to melt the oil.

31. The microencapsulation process of claim 28, wherein the mixer comprises a heated jacket, and wherein the heated jacket heats the mixer sufficiently to melt the vegetable oil upon addition of the oil to the mixer.

32. The microencapsulation process of claim 28, wherein the core material is selected from the group consisting of ace-inhibitors; anti-anginal drugs; anti-arrhythmias; anti-asthmatics; anti-cholesterolemics; anti-convulsants; anti-depressants; anti-diarrhea preparations; anti-histamines; anti-hypertensive drugs; anti-infectives; anti-inflammatory agents; anti-lipid agents; anti-manics; anti-nauseants, anti-stroke agents; anti-thyroid preparations; anti-tumor drugs; anti-tussives; anti-uricenic drugs; anti-viral agents; acne drugs; alkaloids; amino acid preparations; anabolic drugs; analgesics; anesthetics; angiogenesis inhibitors; antacids; antiarthritics; antibiotics; anticoagulants; antiemetics; anti-obesity drugs; antiparasitics; antipsychotics; antipyretics; antispasmodics; antithrombotic drugs; anxiolytic agents; appetite stimulants; appetite suppressants; beta blocking agents; bronchodilators; cardiovascular agents; cerebral dilators; chelating agents; cholecystokinin antagonists; chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastro-intestinal agents; growth regulators; hormone replacement agents; hyperglycemic agents; hypnotics; hypoglycemic agents; laxatives; migrain treatments; mineral supplements; mucolytics; narcotics; neuroleptics; neuromuscular drugs; NSAIDS; nutritional additives; peripheral vaso-dilators; polypeptides; prostaglandins; psychotropics; renin inhibitors; respiratory stimulants; steroids; stimulants; sympatholytics; thyroid preparations; tranquilizers; uterine relaxants; vaginal preparations; vaso-constrictors; vaso-dilators; vertigo agents; vitamins; wound healing agents; botanical substances; fungicides; fertilizers, niacin; L-arginine; creatine monohydrate, L-carnitine, aspirin, loratidine; lovastatin; vitamin C; garlic powder; polygonum cuspidatum root extrart; astaxanthin; tocotrienol and co-enzyme Q-10.

33. The microencapsulation process of claim 28, wherein the vegetable oil is a hydrogenated soy oil with a melting point of about 160 degrees F.

34. The microencapsulation process of claim 28, wherein the vegetable oil is present in an amount from 3% to 30% by weight in the finished microencapsulated particle.

35. The microencapsulation process of claim 28, wherein the vegetable oil is present in an amount from 3% to 20% by weight in the finished microencapsulated particle.

36. The microencapsulation process of claim 28, wherein the vegetable oil is present in an amount from 3% to 10% by weight in the finished microencapsulated particle.

37. The microencapsulation process of claim 28, wherein mixing the core material and the vegetable oil further comprises mixing a sugar or a mineral with the core material and the vegetable oil.

38. The microencapsulation process of claim 37, wherein the sugar is present in the melt from 1–30% by weight of finished microencapsulated particles.

39. The microencapsulation process of claim 37, wherein the sugar is selected from the following; sucrose, dextrose, lactose, polydextrose, maltodextrin, and maltose.

40. The microencapsulation process of claim 37, wherein the mineral is present in the melt from 1–20% by weight of the finished microencapsulated particles.

41. A sustained-release pharmaceutical composition for oral delivery comprising a microencapsulated core material, wherein the microencapsulated core material is microencapsulated by a formulation that consists of an animal or vegetable oil with a melting point above about 110 Deg. F., wherein the animal or vegetable oil is present at from 3% to 20% by weight of the sustained-release pharmaceutical composition, said sustained-release pharmaceutical composition being present in an oral dosage form.

42. The pharmaceutical composition of claim 41, wherein the core material is selected from the group consisting of ace-inhibitors; anti-anginal drugs; anti-arrhythmias; anti-asthmatics; anti-cholesterolemics; anti-convulsants; anti-depressants; anti-diarrhea preparations; anti-histamines; anti-hypertensive drugs; anti-infectives; anti-inflammatory agents; anti-lipid agents; anti-manics; anti-nauseants; anti-stroke agents; anti-thyroid preparations; anti-tumor drugs; anti-tussives; anti-uricernic drugs; anti-viral agents; acne drugs; alkaloids; anabolic drugs; analgesics; anesthetics; angiogenesis inhibitors; antacids; antiarthritics; antibiotics; anticoagulants; antiemetics; antiobesity drugs; antiparasitics; antipsychotics; antipyretics; antispasmodics; antithrombotic drugs; anxiolytic agents; appetite stimulants; appetite suppressants; beta blocking agents; bronchodilators; cardiovascular agents; cerebral dilators; chelating agents; cholecystokinin antagonists; chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastrointestinal agents; growth regulators; hormone replacement agents; hyperglycemic agents; hypnotics; hypoglycemic agents; laxatives; migrain treatments; mineral supplements; mucolytics; narcotics; neuroleptics; neuromuscular drugs; NSAIDS; nutritional additives; peripheral vaso-dilators; polypeptides; prostaglandins; psychotropics; renin inhibitors; respiratory stimulants; steroids; stimulants; sympatholytics; thyroid preparations; tranquilizers; uterine relaxants; vaginal preparations; vaso-constrictors; vasodilators; vertigo agents; vitamins; wound healing agents; botanical substances; fungicides; fertilizers; niacin; L-arginine; creatine monohydrate; L-carnitine; aspirin; loratidine; lovastatin; vitamin C; garlic powder; polygonum cuspidatum root extract; astaxanthin; tocotrienol and co-enzyme Q-10.

43. The pharmaceutical composition of claim 41, wherein the oil having a melting point above about 110 Deg. F. comprises a vegetable oil with a melting point between 120 degrees F. and 200 degrees F.

44. The pharmaceutical composition of claim 41, wherein the oil having a melting point above about 110 Deg. F. is a hydrogenated soy oil with a melting point of about 160 degrees F.

45. The pharmaceutical composition of claim 41, wherein the oil having a melting point above about 110 Deg. F. is present in an amount from 3% to 10% by weight in the sustained-release pharmaceutical composition.

46. A sustained-release pharmaceutical composition for oral delivery comprising a microencapsulated core material, wherein the microencapsulated core material is microencapsulated by a formulation that consists of a sugar or a mineral and an animal or vegetable oil with a melting point above about 110 Deg. F., wherein the animal or vegetable oil is present at from 3% to 20% by weight of the sustained-release pharmaceutical composition, said sustained-release pharmaceutical composition being present in an oral dosage form.

47. The pharmaceutical composition of claim 46, wherein the sugar is present in the melt from 1–30% by weight of sustained-release pharmaceutical composition.

48. The pharmaceutical composition of claim 46, wherein the sugar is selected from the following; sucrose, dextrose, lactose, polydextrose, maltodextrin, and maltose.

49. The pharmaceutical composition of claim 46, wherein the mineral is present in the melt from 1–20% by weight of sustained-release pharmaceutical composition.

50. The pharmaceutical composition of claim 41, wherein the animal or vegetable oil is soy oil having a maximum iodine value of 5.0.

* * * * *